United States Patent
Sekiya

(10) Patent No.: US 8,916,818 B2
(45) Date of Patent: Dec. 23, 2014

(54) CHROMATOGRAPH TANDEM QUADRUPOLE MASS SPECTROMETER

(71) Applicant: Shimadzu Corporation, Kyoto-shi, Kyoto (JP)

(72) Inventor: Marie Sekiya, Otsu (JP)

(73) Assignee: Shimadzu Corporation, Kyoto-Shi (JP)

( * ) Notice: Subject to any disclaimer, the term of this patent is extended or adjusted under 35 U.S.C. 154(b) by 0 days.

(21) Appl. No.: 13/866,654

(22) Filed: Apr. 19, 2013

(65) Prior Publication Data

US 2014/0014833 A1   Jan. 16, 2014

(30) Foreign Application Priority Data

Apr. 20, 2012   (JP) .................................. 2012-096837

(51) Int. Cl.
| | |
|---|---|
| H01J 49/42 | (2006.01) |
| G01N 27/62 | (2006.01) |
| G01N 30/72 | (2006.01) |
| G01N 30/86 | (2006.01) |
| H01J 49/00 | (2006.01) |

(52) U.S. Cl.
CPC ............ *G01N 30/72* (2013.01); *G01N 30/8651* (2013.01); *G01N 30/8675* (2013.01); *H01J 49/0045* (2013.01); *G01N 30/8658* (2013.01)
USPC ......................................... 250/282; 250/281

(58) Field of Classification Search
USPC ................................................ 250/281, 282
See application file for complete search history.

(56) References Cited

U.S. PATENT DOCUMENTS

| | | | | |
|---|---|---|---|---|
| 5,313,061 | A  * | 5/1994 | Drew et al. .................... | 250/281 |
| 6,865,926 | B2 * | 3/2005 | O'Brien et al. ............... | 73/23.27 |
| 6,987,261 | B2 * | 1/2006 | Horning et al. ............... | 250/282 |
| 7,071,464 | B2 * | 7/2006 | Reinhold ....................... | 250/282 |
| 7,240,038 | B2 * | 7/2007 | Hitt .................................. | 706/12 |
| 7,473,892 | B2 * | 1/2009 | Sano et al. ..................... | 250/281 |
| 7,548,818 | B2 * | 6/2009 | Kieser ............................ | 702/22 |

(Continued)

FOREIGN PATENT DOCUMENTS

| | | |
|---|---|---|
| JP | 2011-249109 | 12/2011 |
| WO | WO 2007/102201 A1 | 9/2007 |

OTHER PUBLICATIONS

Examination Report received for Chinese Patent Application No. 201310138953.X mailed on May 21, 2014, 12 pages. (5 pages of English Translation and 7 pages of Office Action).

(Continued)

*Primary Examiner* — David A Vanore
(74) *Attorney, Agent, or Firm* — Bingham McCutchen LLP

(57) ABSTRACT

A chromatograph tandem quadrupole mass spectrometer is provided for capable of easily and accurately setting the measurement conditions for a product ion scan measurement to determine the parameters of an MRM measurement for many compounds. When an analyst selects a compound or compounds to be MRM-measured, the data processor collects the information on the selected compounds, sets the time range in which a predetermined time width is added before and after the retention time of each compound as the measurement time range, sets the m/z associated with each compound as the m/z of the precursor ion, and obtains the m/z range of the product ion scan from the m/z of the precursor ion. The data processor automatically creates and displays a measurement condition table in which the data are arranged in order. The analyst appropriately modifies the values if necessary to complete the measurement condition table.

8 Claims, 4 Drawing Sheets

(56) References Cited

U.S. PATENT DOCUMENTS

| | | | |
|---|---|---|---|
| 7,621,171 B2* | 11/2009 | O'Brien | 73/23.41 |
| 7,880,135 B2* | 2/2011 | Umemura | 250/281 |
| 7,884,318 B2* | 2/2011 | Milgram et al. | 250/282 |
| 7,919,745 B2* | 4/2011 | Shilov et al. | 250/281 |
| 7,932,486 B2* | 4/2011 | Sano et al. | 250/281 |
| 8,153,961 B2* | 4/2012 | Zabrouskov | 250/282 |
| 8,198,585 B2* | 6/2012 | Yamaguchi | 250/288 |
| 8,507,844 B2* | 8/2013 | Mazza | 250/282 |
| 2013/0240723 A1* | 9/2013 | Bonner et al. | 250/282 |
| 2013/0289893 A1* | 10/2013 | Kawase | 702/23 |

OTHER PUBLICATIONS

"Scheduled MRM™ Algorithm Tutorial", MDS Inc. and Applied Biosystems Inc., Document No. D1 000066785 B, Oct. 2008, pp. 1-12.

* cited by examiner

Fig. 4A

COMPOUND INFORMATION TABLE

| COMPOUND NAME | RETENTION TIME (min.) | m/z 1 | m/z 2 |
|---|---|---|---|
| COMPOUND A | 10.3 | 100 | 200 |
| COMPOUND B | 10.9 | 110 | 210 |
| COMPOUND C | 11.3 | 30 | 35 |

Fig. 4B 

MEASUREMENT CONDITION TABLE

| COMPOUND NAME | MEASUREMENT INITIATION TIME (min.) | MEASUREMENT TERMINATION TIME (min.) | PRECURSOR ION m/z | SCAN INITITATION m/z | SCAN TERMINATION m/z |
|---|---|---|---|---|---|
| COMPOUND A | 10.0 | 11.0 | 100 | 50 | 115 |
| COMPOUND A | 10.0 | 11.0 | 200 | 50 | 215 |
| COMPOUND B | 10.0 | 12.0 | 110 | 50 | 125 |
| COMPOUND B | 10.0 | 12.0 | 210 | 50 | 225 |
| COMPOUND C | 11.0 | 12.0 | 30 | 15 | 45 |
| COMPOUND C | 11.0 | 12.0 | 35 | 15 | 50 |

Fig. 5A

COMPOUND INFORMATION TABLE

| COMPOUND NAME | RETENTION TIME (min.) | m/z 1 | m/z 2 | MEASUREMENT |
|---|---|---|---|---|
| COMPOUND A | 10.3 | 100 | 200 | ☑ |
| COMPOUND B | 10.9 | 110 | 210 | ☐ |
| COMPOUND C | 11.3 | 30 | 35 | ☑ |

Fig. 5B 

MEASUREMENT CONDITION TABLE

| COMPOUND NAME | MEASUREMENT INITIATION TIME (min.) | MEASUREMENT TERMINATION TIME (min.) | PRECURSOR ION m/z | SCAN INITITATION m/z | SCAN TERMINATION m/z |
|---|---|---|---|---|---|
| COMPOUND A | 10.0 | 11.0 | 100 | 50 | 115 |
| COMPOUND A | 10.0 | 11.0 | 200 | 50 | 215 |
| COMPOUND C | 11.0 | 12.0 | 30 | 15 | 45 |
| COMPOUND C | 11.0 | 12.0 | 35 | 15 | 50 |

CHROMATOGRAPH TANDEM QUADRUPOLE MASS SPECTROMETER

TECHNICAL FIELD

The present invention relates to a chromatograph tandem quadrupole mass spectrometer which combines a chromatograph, such as a gas chromatograph (GC) or a liquid chromatograph (LC), with a tandem quadrupole mass spectrometer (which is also called a triple quadrupole mass spectrometer).

BACKGROUND ART

An MS/MS analysis (tandem analysis) is widely used as a mass analysis method for the identification, structure analysis, quantitative determination, and other measurements of a compound having a large molecular weight. There are a variety of types of mass spectrometers for performing an MS/MS analysis. Among those, a tandem quadrupole mass spectrometer has a relatively simple device structure and is easy to operate and handle.

In a general tandem quadrupole mass spectrometer, ions originating from sample components which are generated in an ion source are introduced into an anterior quadrupole mass filter, where ions that have a specific mass-to-charge ratio m/z are selected as precursor ions. The precursor ions are introduced into a collision cell in which a quadrupole (or multipole for more than four poles) ion guide is provided. A collision induced dissociation (CID) gas such as argon is supplied to the inside of the collision cell. The precursor ions collide with the CID gas and are dissociated in the collision cell. As a result, a variety of product ions are generated. The product ions are introduced into a posterior quadrupole mass filter, where product ions that have a specific mass-to-charge ratio m/z are selected. The selected ions arrive at a detector to be detected.

A tandem quadrupole mass spectrometer as previously described is sometimes used alone, but it is often used in combination with a chromatograph such as a gas chromatograph (GC) or a liquid chromatograph (LC). Especially in recent years, chromatograph tandem quadrupole mass spectrometers have become essential in the field of microanalysis for analyzing a sample containing a number of compounds or a sample in which a variety of impurities are mixed, e.g. the detection of residual pesticides in food, the examination of environmental pollutants, the examination of drug levels in blood, and drug/toxicity screenings.

An MS/MS analysis in a chromatograph tandem quadrupole mass spectrometer includes several measurement modes such as an MRM (Multiple Reaction Monitoring) measurement mode, a precursor ion scan measurement mode, a product ion scan measurement mode, and a neutral loss scan measurement mode (refer to Patent Document 1). Of these, in an MRM measurement mode, the mass-to-charge ratio of the ions which are allowed to pass through the anterior quadrupole mass filter and that of the ions which are allowed to pass through the posterior quadrupole mass filter are fixed so that the intensity (amount) of the specific product ions generated by means of the dissociation of specific precursor ions is measured. Therefore, in an MRM measurement, two-stage mass filters eliminate non-measurement components, and ions and neutral particles derived from impurity components, this enabling the acquisition of an ion intensity signal with a high SN ratio. Therefore, an MRM measurement is a powerful technique, especially for the quantitative analysis of minor components. For example, in a gas chromatograph tandem quadrupole mass spectrometer (GC/MS/MS), an MRM measurement is often used for a simultaneous multicomponent quantitative analysis of residual pesticides and other analyses in which the quantitativity of the components is minute.

Performing an MRM measurement as previously described requires an appropriate setting of, prior to performing an analysis, the measurement conditions such as the mass-to-charge ratio of the precursor ions for the compounds to be measured, the mass-to-charge ratio of the product ions, and the collision energy in a CID operation. In a conventional chromatograph tandem quadrupole mass spectrometer, a product ion scan measurement mode is used to search measurement conditions (measurement parameters) of an MRM measurement. In the product ion scan measurement mode, the mass-to-charge ratio selected for the anterior quadrupole mass filter is fixed, while the mass-to-charge ratio of the ions which are allowed to pass through the posterior quadrupole mass filter is scanned across a predetermined range. More specifically, the measurement conditions of an MRM measurement are determined as in the following manner.

(1) First, in a chromatograph tandem quadrupole mass spectrometer, a simple scan measurement without a CID operation is repeated on a sample which contains a target compound so as to collect the mass spectrum data for a predetermined time range.

(2) Based on the collected data, a mass spectrum, a total ion chromatogram, or a mass chromatogram is created. An analyst analyzes it to obtain the retention time of the target compound and the mass-to-charge ratio which characterizes the target compound.

(3) Subsequently, a product ion scan measurement is performed on the sample which contains the target compound in a predetermined time range near the retention time of the compound so as to repeatedly collect the $MS^2$ spectrum data. In the product ion scan measurement, the mass-to-charge ratio which characterizes the compound is specified as the mass-to-charge ratio of the precursor ions. In the $MS^2$ spectrum, peaks corresponding to a variety of product ions originating from the target compound are observed.

(4) When the collision energy is changed, the mode of the dissociation is changed, which consequently changes the pattern of the observed product ions. In view of this, every time the collision energy is changed by a predetermined level, the product ion scan measurement as described in Step (3) is performed to collect the $MS^2$ spectrum data. Then the analyst examines the $MS^2$ spectrum data to determine the appropriate value of the mass-to-charge ratio for the product ions corresponding to the target compound and the value of the collision energy. The determined values are set as the MRM measurement conditions.

When performing a simultaneous multicomponent quantitative analysis, it is necessary to set beforehand the MRM measurement conditions for all the compounds to be quantitatively determined. This requires the measurement and data processing of Steps (3) and (4) for each of the components. Therefore, each compound requires an appropriate determination of the measurement time range in which a product ion scan measurement is performed, and of the mass-to-charge ratio range across which a scan is performed in the product ion scan measurement. However, in a simultaneous multicomponent analysis, it is not unusual that the number of target compounds is 100 or more. In such cases, it is a troublesome and heavy burden for the analyst to determine the appropriate measurement time range and mass-to-charge ratio range for each of the compounds and to manually enter the determined values.

In the case where two compounds have retention times close to each other, for example, if one end of the measurement time range for a product ion scan measurement is placed between the two peaks, the peaks of the chromatogram will appear very close to the end of the measurement time range. In this case, even a minor shift of the retention time when a measurement sample is actually measured causes the end of the measurement time range to enter the peak range of the chromatogram. This might impede the acquisition of the correct $MS^2$ spectrum and the extraction of appropriate product ions. An appropriate setting of the measurement time range of the product ion scan measurement is required in order to avoid this problem. However, this is a very difficult operation.

For a general chromatograph mass spectrometer, Patent Document 2 discloses a technique aiming to reduce the time and labor for setting the measurement conditions for a scan/SIM (Selected Ion Monitoring) simultaneous measurement. However, the technique described in Patent Document 2 is used for determining the measurement time range and other values for a scan/SIM simultaneous measurement using a general chromatograph mass spectrometer, not a tandem quadrupole mass spectrometer. Hence, the technique is not suitable for determining the measurement conditions for a product ion scan measurement for the sake of the determination of the MRM measurement parameters by means of a chromatograph tandem quadrupole mass spectrometer.

BACKGROUND ART DOCUMENT

Patent Documents

[Patent Document 1] JP-A 2011-249109
[Patent Document 2] WO-A 2007-102201

DISCLOSURE OF THE INVENTION

Problems to be Solved by the Invention

The present invention has been achieved to solve the aforementioned problems, and the main objective thereof is to provide a chromatograph tandem quadrupole mass spectrometer capable of easily, efficiently, and accurately setting the measurement conditions for a product ion scan measurement which is performed to determine the MRM measurement parameters.

Means for Solving the Problems

To solve the aforementioned problems, the present invention provides a chromatograph tandem quadrupole mass spectrometer in which a variety of components contained in a sample are temporally separated by a chromatograph unit and the components are introduced into a tandem quadrupole mass analysis unit for an MS/MS analysis, the chromatograph tandem quadrupole mass spectrometer being capable of performing a product ion scan measurement, including:

a) a compound information memory in which compound information is stored, the compound information including, as information on a compound to be analyzed, a name of the compound, a retention time of the compound, and a mass-to-charge ratio which characterizes the compound; and b) a measurement condition table creator for creating a measurement condition table which specifies, as measurement conditions for a product ion scan measurement which is performed to determine an MRM measurement parameters, at least a measurement time range for performing the product ion scan measurement, a mass-to-charge ratio of a precursor ion in the product ion scan measurement, and a mass-to-charge ratio range to be scanned in the product ion scan measurement, wherein the measurement condition table for all or part of compounds which are registered in the compound information table stored in the compound information memory is created by setting a mass-to-charge ratio associated with each compound as the aforementioned mass-to-charge ratio of the precursor ion, a mass-to-charge ratio range which is computed based on the mass-to-charge ratio of the precursor ion as the aforementioned mass-to-charge ratio range to be scanned, and a time range in which a predetermined temporal width is added before and after a retention time associated with each compound as the aforementioned measurement time range.

In the chromatograph tandem quadrupole mass spectrometer according to the present invention, the chromatograph unit is a gas chromatograph or a liquid chromatograph.

In the chromatograph tandem quadrupole mass spectrometer according to the present invention, the compound information table may be created based on information obtained by an analyst or user in a previous measurement of a reference sample containing a target compound. Alternatively, the compound information table may be created using an existing publicly-available compound database. The retention times included in the compound information table may be replaced by retention indexes which are often used in GC.

In the chromatograph tandem quadrupole mass spectrometer according to the present invention, in response to a predetermined instruction from the analyst for example, the measurement condition table creator collects, for all or some specific compounds registered in the compound information table, the information on the retention time and the mass-to-charge ratio which characterizes each of the compounds, and then sets the mass-to-charge ratio as the mass-to-charge ratio of the precursor ion of each compound without any modification. Supposing that the valence of the product ions generated by dissociation is only one, the mass-to-charge ratio of the product ions should be smaller than that of the precursor ions. In many cases, the product ions that have a mass-to-charge ratio which is much lower than that of the precursor ions are of little importance. Using an algorithm that considers these factors, the measurement condition table creator computes the mass-to-charge ratio range of the product ions based on the mass-to-charge ratio of the precursor ions, and sets the mass-to-charge ratio range as the mass-to-charge ratio range to be scanned when a product ion scan measurement for the compound is performed. Further, the measurement condition table creator sets the time range obtained by adding a predetermined temporal width before and after the retention time of each compound as the measurement time range for the compound.

As described above, the measurement condition table creator automatically creates a measurement condition table in which the measurement time range of the product ion scan measurement, the mass-to-charge ratio of the precursor ions, and the mass-to-charge ratio range for performing the product ion scan are defined, and displays the table in a window of a display, for example. However, the measurement condition table automatically created as just described does not always reflect the intention of the analyst. Especially when the retention times of a plurality of compounds are temporally close, it is possible that an end of the measurement time range is placed at an inappropriate position. Given this factor, it is preferable that the analyst is allowed to appropriately modify the measurement condition table created as described above.

Preferably, the compound information table includes all the possible compounds which will be set as an analysis target by the analyst or user. However, all the compounds are not always set as the compounds to be analyzed in an analysis of a sample. Rather, in general, only some compounds among many compounds registered in the compound information table are set as the analysis targets in an analysis.

In consideration of those factors, it is preferable that the chromatograph tandem quadrupole mass spectrometer according to the present invention may further include:

c) a display controller for displaying the compound information table in a window of a display; and d) a selection unit for allowing an analyst to select a compound for which the product on scan is to be performed in the compound information table displayed in the window of the display, wherein:

the measurement condition table creator selects only the compound selected by the selection unit in the compound information table and creates the measurement condition table so that a product ion scan measurement is performed in which the mass-to-charge ratio corresponding to the compound is set as the mass-to-charge ratio of the compound.

A variety of selection methods are possible for the selection unit. As an aspect thereof, the selection unit may allow the analyst to select a compound by placing a checkmark in a checkbox provided for each compound in the compound information table. This facilitates the selection operation and the selection result is visually understandable.

Also in the case where the compound information table includes, as the information on the compound to be analyzed, the mass-to-charge ratio of the precursor ion which characterizes the compound and the mass-to-charge ratios of the product ions generated by the dissociation of the precursor ion, the measurement condition table creator may preferably set the mass-to-charge ratio of the precursor ion which is associated with each compound in the compound information table as the mass-to-charge ratio of the precursor ions in the measurement condition table. In this case, the mass-to-charge ratio range for the product ion scan may be determined by ignoring the mass-to-charge ratios of the product ions which are associated with each compound in the compound information table. This allows, in the case of somewhat inappropriate mass-to-charge ratios of the product ions associated with each compound in the compound information table, a performance of an MRM measurement using more appropriate mass-to-charge ratios of the product ions.

In the chromatograph tandem quadrupole mass spectrometer according to the present invention, the measurement condition table creator may preferably provide, in the measurement condition table, fields in which the names of the compounds included as the information in the compound information table are entered. This makes the compounds corresponding to the measurement conditions understandable at a glance when the analyst examines the MRM measurement parameters, which enhances the analyst's working efficiency.

While the analyst grasps the relationship between each measurement time range and the retention time of each compound in the measurement condition table or modifies the measurement condition table, if a chromatogram (total ion chromatogram) is displayed on the same operation window, the analyst can refer to it. This facilitates operation and decreases operational mistakes. In view of this, in the chromatograph tandem quadrupole mass spectrometer according to the present invention, the display controller may display, in the same window in which the compound information table and the measurement condition table are displayed, a chromatogram which includes, at the least, the presence of a peak corresponding to the compound included in the measurement condition table. In addition, information that enables the analyst to know the measurement time range which corresponds to each compound may be preferably superimposed on the chromatogram.

When the measurement time range in the measurement condition table is modified as previously described, graphical modification on the chromatograph which is being displayed improves work efficiency and yields fewer mistakes than deleting and reentering values in the table by key strokes. In view of this, the measurement time range for performing a product ion scan which is superimposed on the chromatogram may be graphically modified by an instruction provided through a pointing device.

When computing the mass-to-charge ratio range of the product ions based on the mass-to-charge ratio of the precursor ions, the measurement condition table creator may set a predetermined mass-to-charge ratio as the lower limit and set the mass-to-charge ratio obtained by adding a predetermined value to or subtracting a predetermined value from the mass-to-charge ratio of the precursor ions as the upper limit. In this case, a plurality of predetermined values are prepared in advance for the mass-to-charge ratio which is used as the lower limit. One predetermined value may be selected from among the plurality of predetermined values depending on the mass-to-charge ratio of the precursor ions so that the selected predetermined value does not exceed the mass-to-charge ratio.

Since the product ions appropriate for an MRM measurement depend on the collision energy, the measurement condition table creator may create a measurement condition table for each of different collision energies. With this configuration, when the optimum value of the collision energy for an MRM measurement is searched under the conditions of a collision energy, the scan control of the mass-to-charge ratio and other operations can be performed using one corresponding measurement condition table. This simplifies the operation and also yields fewer mistakes when modifying the measurement condition table and in other operations.

Effects of the Invention

The chromatograph tandem quadrupole mass spectrometer according to the present invention can save an analyst much labor in terms of the input operation required to set the measurement conditions for performing a product ion scan measurement which is performed to determine the conditions for an MRM measurement. This can ease the burden of the analyst and also prevent inputting errors from occurring. In addition, since the appropriate precursor ion and the appropriate mass-to-charge ratio range of the product ions are set for each compound, the precursor ion and product ions which are suitable for a quantitative analysis can be set as MRM measurement parameters for each compound. Further, since an irrelevant mass-to-charge ratio range is not scanned when performing a product ion scan measurement, the measurement time can be shortened.

BRIEF DESCRIPTION OF THE DRAWINGS

FIGS. 4A and 4B show an example of a compound information table and a measurement condition table created from the table, respectively, in the GC/MS/MS according to the present embodiment.

FIGS. 5A and 5B show another example of a compound information table and a measurement condition table created from the table, respectively, in the GC/MS/MS according to the present embodiment.

BEST MODES FOR CARRYING OUT THE INVENTION

Hereinafter, a gas chromatograph tandem quadrupole mass spectrometer (GC/MS/MS), which is an embodiment of the present invention, will be described with reference to the attached figures.

Figure 1:
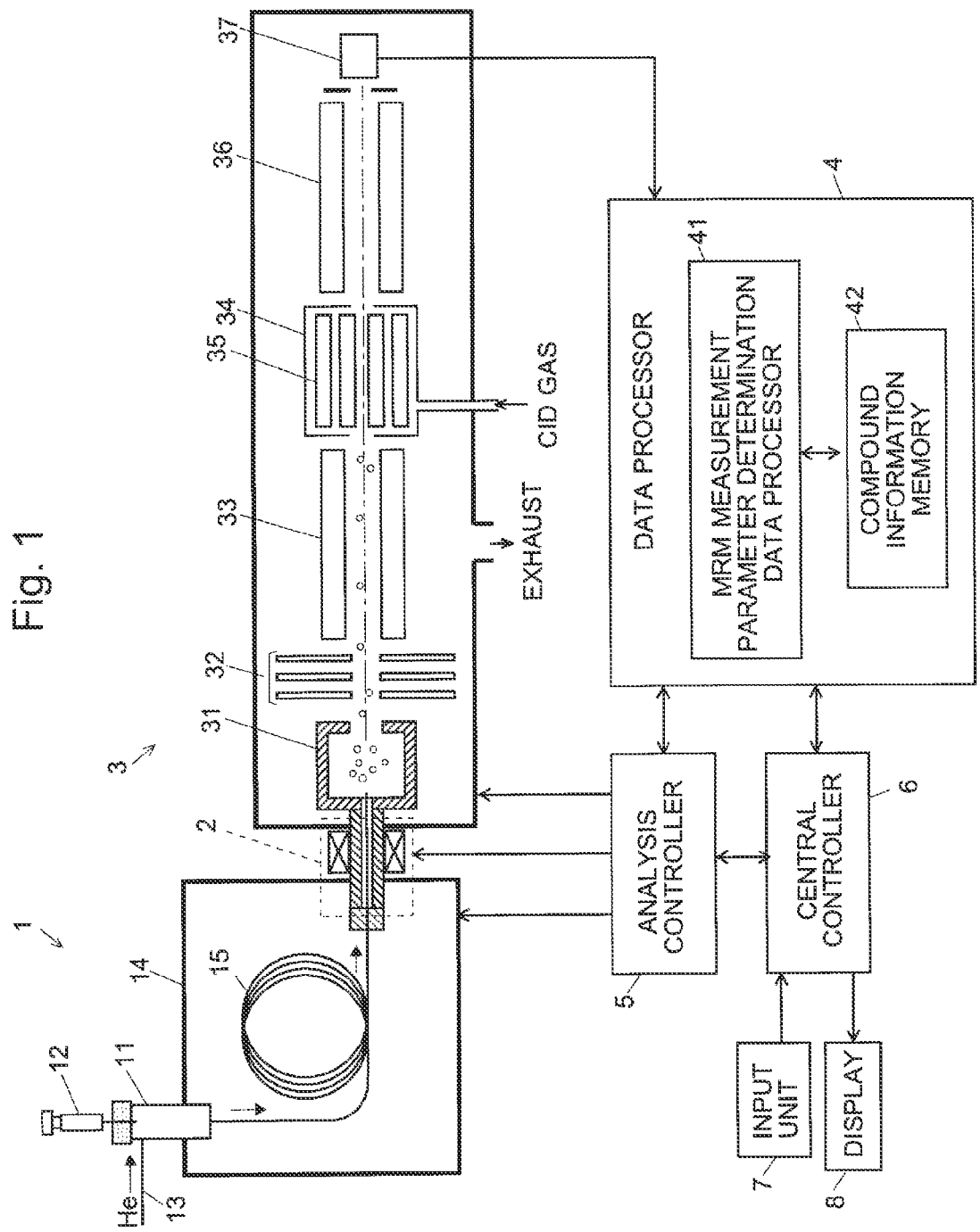
FIG. 1 shows an overall configuration diagram of a GC/MS/MS according to an embodiment of the present invention.

FIG. 1 shows an overall configuration diagram of the GC/MS/MS according to the present embodiment. In a gas chromatograph (GC) unit 1, a sample vaporization chamber 11 is provided at the inlet end of a column 15 which is heated to an appropriate temperature by a column oven 14. A carrier gas is supplied to the sample vaporization chamber 11 through a carrier gas passage 13 at a predetermined flow rate. The carrier gas flows into a column. In this state, when a small amount of liquid sample is injected to the sample vaporization chamber 11 by a micro syringe 12, the liquid sample is immediately evaporated and sent into the column 15 by the flow of a carrier gas. While passing through the column 15, a variety of compounds in the sample gas are temporally separated and arrive at the outlet of the column 15. The compounds pass through an interface unit 2 which includes a heater and other units, and are introduced into an ionization chamber 31 of a mass spectrometer (MS) unit 3.

In the MS unit 3, the compound molecules which have been introduced into the ionization chamber 31 are ionized by an electron ionization (EI) method, a chemical ionization (CI) method, or another method. The generated ions are extracted to the outside of the ionization chamber 31, and are converged by an ion lens 32. Then, the ions are injected into a longitudinal space of an anterior quadrupole mass filter 33 which is composed of four rod electrodes. A voltage in which a direct-current voltage and a radio-frequency voltage are superimposed is applied to the anterior quadrupole mass filter 33 from a power source (not shown). Only ions having the mass-to-charge ratio corresponding to the applied voltage pass through the longitudinal space and are introduced into a collision cell 34.

A multipole ion guide 35 for converging ions by operating the radio-frequency electric field is provided inside the collision cell 34. A CID gas such as Ar gas is continuously or intermittently introduced into the collision cell 34. The ions injected into the collision cell 34 come in contact with the CID gas and are dissociated. Product ions generated by the dissociation are converged and introduced into the longitudinal space of a posterior quadrupole mass filter 36. As the anterior quadrupole mass filter 33, the posterior quadrupole mass filter 36 is composed of four rod electrodes. A voltage in which a direct-current voltage and a radio-frequency voltage are superimposed is applied to the rod electrodes from a power source (not shown). Only product ions having the mass-to-charge ratio corresponding to the applied voltage pass through the longitudinal space and arrive at an ion detector 37.

The detection signal from the ion detector 37 is converted into digital data by an A/D converter (not shown) and the digital data are sent to a data processor 4. The data processor 4 performs a predetermined arithmetic processing and creates a mass spectrum, mass chromatogram, or a total ion chromatogram. Further, the data processor 4 performs a qualitative analysis, a quantitative analysis, and other analyses. In order to perform the processings that are characteristic of the present invention, the data processor 4 includes as functional blocks an MRM measurement parameter determination data processor 41, a compound information memory 42, and other units. The operations of the blocks for the GC unit 1, the interface unit 2, and the MS unit 3 are controlled by an analysis controller 5. An input unit 7 and a display 8 are connected to the central controller 6. The input unit 7 includes a keyboard and a pointing device such as a mouse. In comparison to the analysis controller 5, the central controller 6 controls input/output processing, and governs upper-level basic controls. The data processor 4, the analysis controller 5, and the central controller 6 are realized by executing dedicated control/process software which has been installed in a personal computer as hardware resources.

The GC/MS/MS of the present embodiment can perform an MRM measurement in the MS unit 3 for each of the compounds which have been temporally separated in the GC unit 1. In the MRM measurement, the mass-to-charge ratio of the precursor ions and that of product ions which are set in the measurement can differ for each compound. Performing an accurate and high-sensitive MRM measurement for each compound requires the setting of measurement parameters suitable for each compound, such as the mass-to-charge ratio of the precursor ion, that of the product ions, and the collision energy. Hereinafter, the operation and processing for the setting of the MRM measurement parameters to quantitatively-analyze the compounds in a target sample to be analyzed by means of an MRM measurement using the GC/MS/MS of the present embodiment are described in detail with reference to FIGS. 2, 3, 4A, 4B, 5A, and 5B.

In order to determine the MRM measurement parameters for performing an MRM measurement of a target sample, a product ion scan measurement of the target sample is performed. Hence, it is necessary to determine the measurement conditions for this product ion scan measurement. The determination of the measurement conditions uses a compound information table which has been previously stored in the compound information memory 42. FIG. 4A shows an example of the compound information table. The compound information table contains information on many compounds which may be analyzed by a user of the GC/MS/MS. For each compound, the information includes: the name of the compound (compound name); the retention time under predetermined GC analysis conditions (e.g. the carrier gas flow rate, the temperature profile, and other parameters in the GC unit 1); one or more mass-to-charge ratio values characteristic of the compound; and other values.

Such a compound information table may be provided by the manufacturer of the apparatus. However, since the compounds to be analyzed differ for each user, generally, the user can create a compound information table based on the result of the measurement of a standard sample or the like. An example of the procedure for creating a compound information table is as follows.

First, in the GC unit 1, a standard sample which contains a plurality of known compounds is injected to the sample vaporization chamber 11 and the compounds contained in the standard sample are separated in the column 15 under predetermined separation conditions. In the MS unit 3, without performing a CID operation in the collision cell 34, a simple scan measurement using either the anterior quadrupole mass filter 33 or the posterior quadrupole mass filter 36 is repeated. Based on the obtained data, the data processor 4 creates a total ion chromatogram in which peaks corresponding to the known compounds appear. Then, the data processor 4 obtains the retention times based on the positions of the chromatogram peaks which correspond to the compounds. In addition, the data processor 4 extracts a peak that has a large signal intensity, for example, in a mass spectrum or in the mass spectrum obtained by adding a plurality of mass spectra during the period in which the peaks appear, thereby obtaining the mass-to-charge ratios which characterize the compounds. By collecting the retention times and mass-to-charge ratios as obtained in the manner as just described and organizing them for each compound, a compound information table can be created automatically. It is evident that such a compound information table does not necessarily have to be created for every measurement of a target sample, but rather previously created tables can be reused in the case where the same GC analysis conditions are used.

Figure 2:
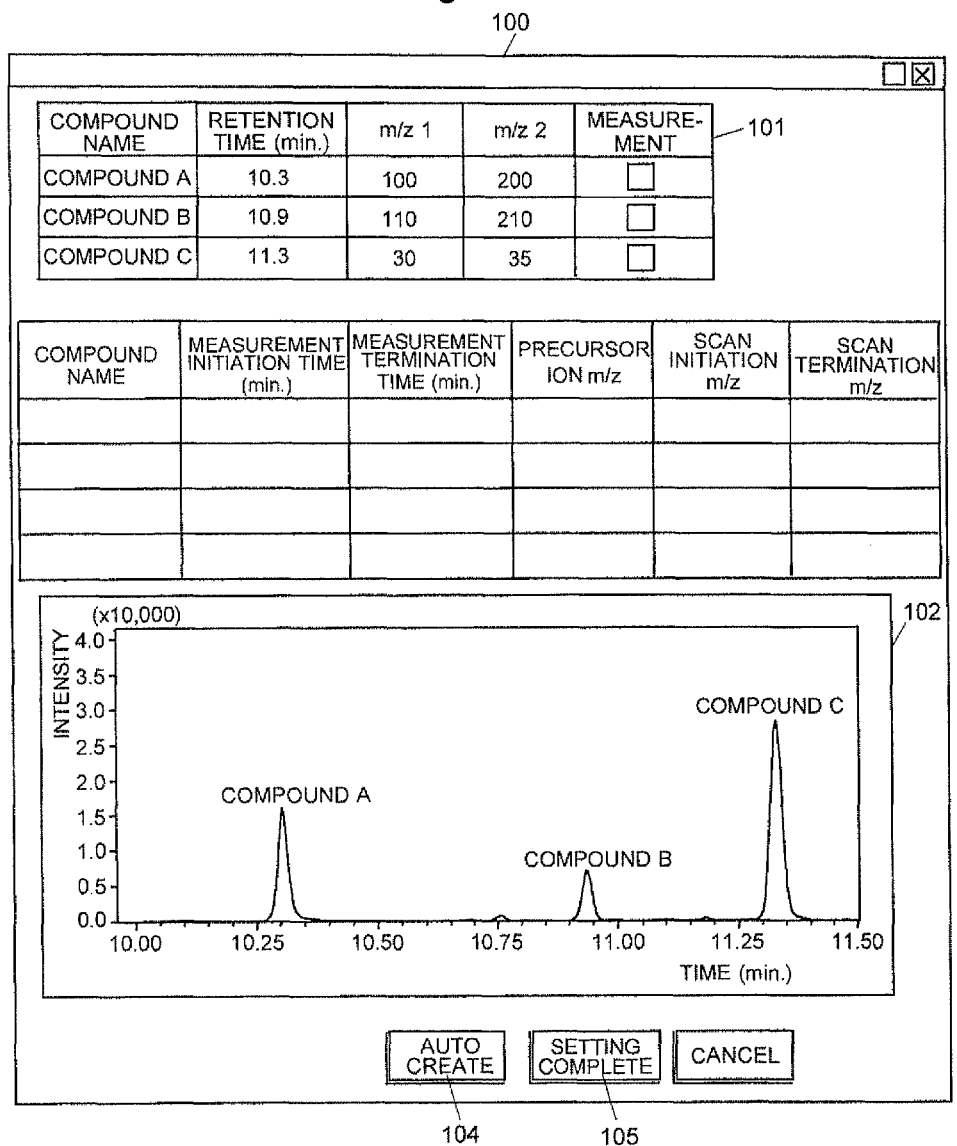
FIG. 2 shows an example of a measurement condition table setting window for setting the MRM measurement parameters in the GC/MS/MS according to the present embodiment.

Prior to the measurement of the target sample, the analyst enters, through the input unit, an instruction of creating a measurement condition table which defines the measurement conditions for the product ion scan measurement for the determination of the MRM measurement parameters. Upon receiving this instruction, an MRM measurement parameter determination data processor 41 is operated by the data processor 4 so as to display a measurement condition table setting window 100 on a window of the display 8 as shown in FIG. 2. A compound information table 101 and a reference chromatogram 102 are included in the measurement condition table setting window 100. In the compound information table 101 which is shown in this example, a checkbox is provided for each of the compounds in the compound information table shown in FIG. 4A. The compound information table 101 in FIG. 2 is the same as FIG. 5A. The total ion chromatogram obtained by measuring the standard sample as described above may be used as the reference chromatogram 102. In the reference chromatogram 102, in order to clearly show the corresponding relationship between each of the compounds (compounds A, B, and C in this example) listed in the compound information table 101 and each peak on the reference chromatogram 102, the compound names which are listed in the compound information table 101 are shown near their corresponding peaks.

Figure 3:
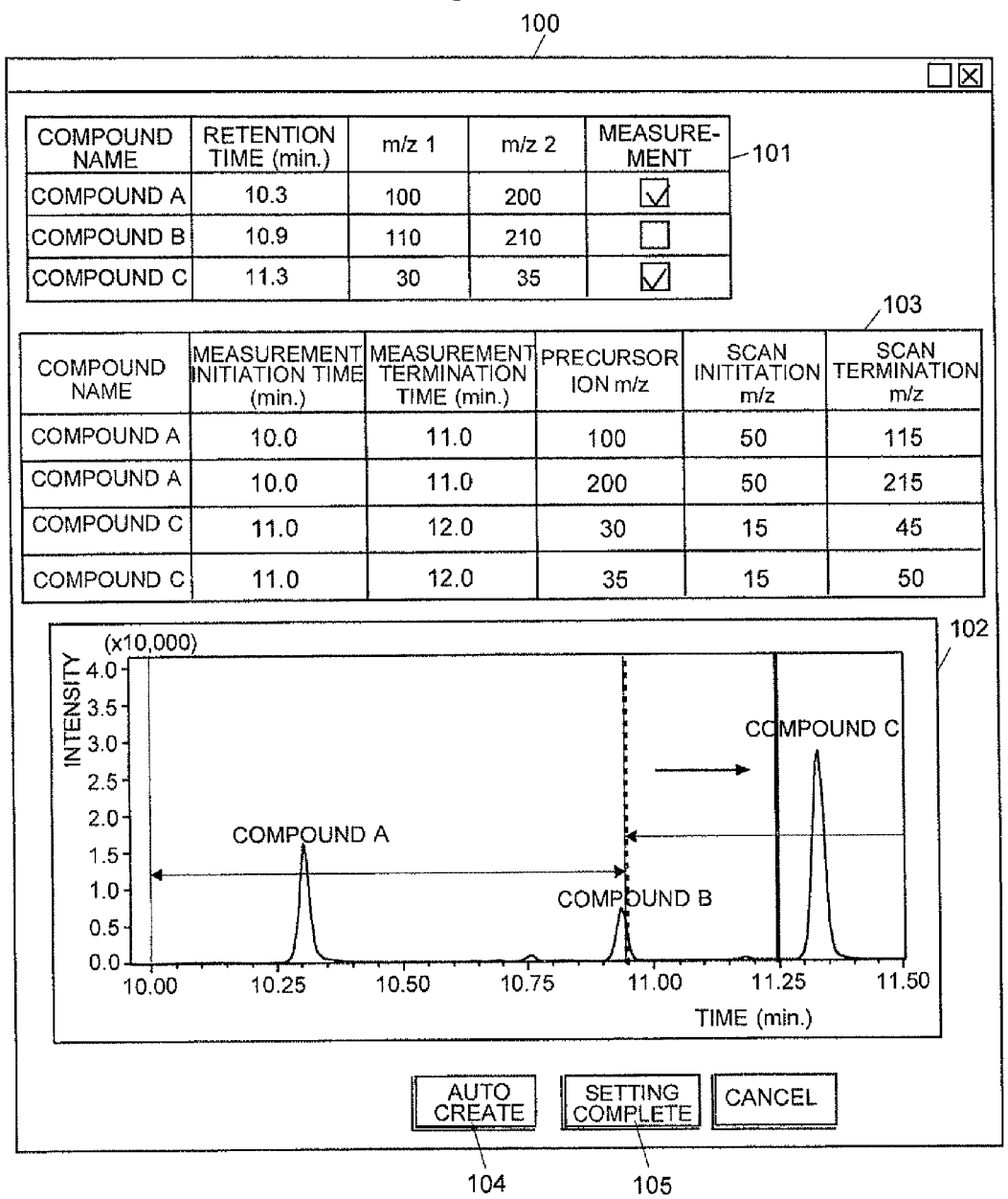
FIG. 3 shows an example of the measurement condition table setting window after a measurement condition table is automatically created.

While referring to the reference chromatogram 102 in the measurement condition table setting window 100 to understand the positions of the peaks, the analyst selects a compound or compounds to be quantitatively-measured by an MRM measurement, i.e. the analyst places a checkmark in the checkbox in the rightmost column of the compound information table 101. In the examples of FIG. 3 and FIG. 5A, compound A and C are selected.

After selecting the compounds, the analyst clicks an "Auto Create" button 104 so as to enter the instruction of the creation of a measurement condition table. Upon receiving this instruction, the MRM measurement parameter determination data processor 41 extracts the retention time and the mass-to-charge ratios of the selected compounds from the compound information table 101. After that, for each compound, the MRM measurement parameter determination data processor 41 determines the measurement time range in which a predetermined time width is added before and after the retention time, and obtains the initiation point (measurement initiation time) and the termination point (measurement termination time) of the measurement time range. In this example, the measurement time range is determined so that 0.2 minutes or more of time period is added before and after the retention time, and the initiation point and the termination point are determined in steps of one minute. That is, the measurement time range for the compound A whose retention time is 10.3 minutes is 10 through 11 minutes, with the measurement initiation time of 10 minutes and the measurement termination time of 11 minutes. Naturally, the time range corresponding to a retention, time can be appropriately changed, and any method for determining the time range can be used as long as the determined measurement time range includes the retention time.

In addition, the MRM measurement parameter determination data processor 41 sets all the mass-to-charge ratios associated with each of the selected compounds as the mass-to-charge ratios of the precursor ions which correspond to the compound. Therefore, 100 and 200 are set as the mass-to-charge ratios of the precursor ions of the compound A, for example. Further, based on the values of the mass-to-charge ratios of the precursor ions, the MRM measurement parameter determination data processor 41 computes the range for performing a mass-to-charge ratio scan in the posterior quadrupole mass filter 36 when a product ion scan measurement is performed.

Suppose that all the product ions generated by dissociation are monovalent, in other words, suppose that multivalent ions are not generated, the mass-to-charge ratios of the product ions should be smaller than those of the precursor ions. In particular, multivalent ions are rarely generated in an ion source, especially in the electron ionization (EI) method, which is often used in a GC/MS; therefore, such an assumption of valence is valid. In general, the product ions having a mass-to-charge ratio which is considerably lower than that of the precursor ions are of little importance. Using an algorithm that considers these factors, the upper limit and the lower limit of the mass-to-charge ratio of the product ions may be determined.

In this example, the value in which "15" is added to the mass-to-charge ratio of the precursor ions is set as the upper limit of the mass-to-charge ratio of the product ions, with a margin for measurement errors and other factors. Either "15" or "50" is selected as the lower limit of the mass-to-charge ratio of the product ions. In the case where the value of the mass-to-charge ratio of the precursor ions exceeds 50, "50" is selected as the lower limit, while in the case where the value of the mass-to-charge ratio of the precursor ions is not more than 50, "15" is selected as the lower limit. Therefore, if the mass-to-charge ratio of the precursor ions is 100, for example, the mass-to-charge ratio range of the product ions will have the upper limit of 115 and the lower limit of 50. Naturally, these values may be appropriately changed, and any method can be used to determine the mass-to-charge ratio range for a mass scan of the mass-to-charge ratio value of the precursor ions.

After determining, for the selected compounds, the measurement time range, the mass-to-charge ratio range of the precursor ions, and the mass-to-charge ratio range for a product ion scan from the compound information table, the MRM measurement parameter determination data processor 41 creates a measurement condition table 103 as shown in FIG. 4B (and FIG. 5B) and displays it in the measurement condition table setting window 100. The measurement time ranges defined in the measurement condition table 103 are superimposed on the reference chromatogram 102.

The measurement condition tables of FIGS. 4B and 5B show that, in the measurement time range from the elapsed time of 10.0 minutes to 11.0 minutes, beginning at the point in time when a sample is injected in the GC unit 1, two product ion scan measurements are alternately performed in a time-sharing manner so that they are performed effectively simultaneously in order to determine the quantity of the compound A; in the first product ion scan measurement, the selected mass-to-charge ratio for the anterior quadrupole mass filter 33 is 100, and the mass scan range for the posterior quadrupole mass filter 36 is 50 through 115; and in the second product ion scan measurement, the selected mass-to-charge ratio for the anterior quadrupole mass filter 33 is 200, and the mass scan range for the posterior quadrupole mass filter 36 is 50 through 215. In addition, in the measurement time range from the elapsed time of 11.0 minutes to 12.0 minutes, two product ion scan measurements are alternately performed in a time-sharing manner so that they are performed effectively simultaneously in order to determine the quantity of the compound C: in the first product ion scan measurement, the selected mass-to-charge ratio for the anterior quadrupole mass filter 33 is 30, and the mass scan range for the posterior quadrupole mass filter 36 is 15 through 45; and in the second product ion scan measurement, the selected mass-to-charge ratio for the anterior quadrupole mass filter 33 is 35, and the mass scan range for the posterior quadrupole mass filter 36 is 15 through 50.

The measurement condition table created as described above does not always reflect the intention of the analyst. For example, in the case where a border of a measurement time range is set extremely close to the initiation point of the termination point of a peak, if the retention time shifts in the MRM measurement for an actual target sample, the data which correspond to a portion of the peak cannot be obtained, which interferes with an accurate quantitative determination. In some cases, the analyst may manually have to modify or change appropriately the measurement condition table 103 which has been automatically created as previously described. Until a setting-complete instruction is entered, which will be described later, the values in the measurement condition table 103 are shown in the text boxes, and the analyst can appropriately change their values by an input operation through the keyboard.

The measurement time range may be graphically modified. That is, in the measurement condition table, a row in which a measurement time range is to be changed is clicked on with a pointing device. For example, suppose that the second row in the measurement condition table 103 shown in FIG. 3 is clicked on. A marker is then shown at the position of the measurement termination time of the specified row in the reference chromatogram 102. By selecting this marker with the pointing device, moving it to a desired position, and then releasing the selection of the marker, the measurement time range is broadened or narrowed to the time which corresponds to the position to which the marker has been moved. Simultaneously, the value of the measurement termination time in the measurement condition table 103 is changed accordingly. In this manner, the measurement time range can be graphically and intuitively modified and changed by operating a pointing device without having to entering a value by means of key strokes.

After the automatically created measurement condition table 103 has been appropriately changed/modified as previously described, if the analyst clicks a "setting complete" button 105, the setting of the measurement condition table 103 is completed. Then, in accordance with the contents of the measurement condition table 103, a measurement condition file for performing a product ion scan measurement is automatically created. Now the measurement for determining the MRM measurement parameters for a target value is ready.

By providing an instruction for performing a measurement, a product ion scan measurement in accordance with the measurement condition file is performed. Then, by using the $MS^2$ obtained from the product ion scan measurement, appropriate product ions can be determined for each compound.

As previously described, when the collision energy is changed, the mode of the dissociation of ions is often changed, which changes the mass-to-charge ratio of the generated product ions. Therefore, in the case where the MRM measurement parameters include the collision energy, it is necessary to also change the mass scan range for the product ion scan measurement for determining the MRM measurement parameters in accordance with the collision energy. Therefore, it is preferable to prepare a measurement condition table for each of the different collision energies. In this case, the number of measurement condition tables is the number of the collision energies. Hence, it is preferable in terms of good operability that the measurement condition tables can be changed on-screen by selecting a tab.

As described thus far, with the GC/MS/MS according to the present embodiment, the measurement condition table for a product ion scan measurement for determining the MRM measurement parameters can be very easily created. This alleviates the burden for the analyst and can prevent an erroneous measurement condition from being set.

In the description of the embodiment, checkboxes are provided in the compound information table 101 which is shown in the measurement condition table setting window 100 so that compounds can be selected. However, as shown in FIG. 4A, a compound information table without checkboxes may be displayed in the measurement condition table setting window 100 and a measurement condition table in which the measurement conditions for all the compounds contained in the compound information table may be created (refer to FIG. 4B).

It should be noted that the embodiment described thus far is an example, and it is evident that any modification, adjustment, or addition made within the spirit of the present invention can be performed.

EXPLANATION OF NUMERALS

1 . . . GC Unit  
11 . . . Sample Vaporization Chamber  
12 . . . Micro Syringe  
13 . . . Carrier Gas Passage  
14 . . . Column Oven  
15 . . . Column  
2 . . . Interface Unit  
3 . . . MS Unit  
31 . . . Ionization Chamber  
32 . . . Ion Lens  
33 . . . Anterior Quadrupole Mass Filter  
34 . . . Collision Cell  
35 . . . Multipole Ion Guide  
36 . . . Posterior Quadrupole Mass Filter  
37 . . . Ion Detector  
4 . . . Data processor  
41 . . . MRM Measurement Parameter Determination Data Processor  
42 . . . Compound Information Memory  
5 . . . Analysis Controller  
6 . . . Central Controller  
7 . . . Input Unit  
8 . . . Display  
100 . . . Measurement Condition Table Setting Window  
101 . . . Compound Information Table 102 . . . Reference Chromatogram
103 . . . Measurement Condition Table
104 . . . "Auto Create" Button
105 . . . "Setting Complete" Button

The invention claimed is:

1. A chromatograph tandem quadrupole mass spectrometer for performing a product ion scan measurement, comprising:
a chromatograph unit in which a variety of components contained in a sample are temporally separated; and
a tandem quadrupole mass analysis unit to which the components are introduced from the chromatograph unit for an MS/MS analysis, said tandem quadrupole mass analysis unit comprising:
a compound information memory in which compound information is stored, the compound information including, as information on a compound to be analyzed, a name of the compound, a retention time of the compound, and a mass-to-charge ratio which characterizes the compound; and
a measurement condition table creator for creating a measurement condition table which specifies, as measurement conditions for a product ion scan measurement which is performed to determine an MRM measurement parameters, at least a measurement time range for performing the product ion scan measurement, a mass-to-charge ratio of a precursor ion in the product ion scan measurement, and mass-to-charge ratio range to be scanned in the product ion scan measurement,
wherein the measurement condition table for all or part of compounds which are registered in the compound information table stored in the compound information memory is created by setting a mass-to-charge ratio associated with each compound as the aforementioned mass-to-charge ratio of the precursor ion, a mass-to-charge ratio range which is computed based on the mass-to-charge ratio of the precursor ion as the aforementioned mass-to-charge ratio range to be scanned, and a time range in which a predetermined temporal width is added before and after a retention time associated with each compound as the aforementioned measurement time range.

2. The chromatograph tandem quadrupole mass spectrometer according to claim 1, further comprising:
a display controller for displaying the compound information table in a window of a display; and
a selection unit for allowing an analyst to select a compound for which the product ion scan measurement is to be performed in the compound information table displayed in the window of the display, wherein:
the measurement condition table creator selects only the compound selected by the selection unit in the compound information table and creates the measurement condition table so that a product ion scan measurement is performed in which the mass-to-charge ratio corresponding to the compound is set as the mass-to-charge ratio of the precursor ion.

3. The chromatograph tandem quadrupole mass spectrometer according to claim 2, wherein the selection unit allows the analyst to select a compound by placing a checkmark in a checkbox provided for each compound in the compound information table.

4. The chromatograph tandem quadrupole mass spectrometer according to claim 2, wherein the display controller displays, in a same window in which the compound information table and the measurement condition table are displayed, a chromatogram in which at least a peak corresponding to the compound included in the measurement condition table is present, and superimposes, on the chromatogram, information that enables the analyst to know the measurement time range which corresponds to each compound.

5. The chromatograph tandem quadrupole mass spectrometer according to claim 4, wherein the measurement time range for performing a product ion scan measurement which is superimposed on the chromatogram can be graphically modified by an instruction provided through a pointing device.

6. The chromatograph tandem quadrupole mass spectrometer according to claim 1, wherein the measurement condition table creator creates a measurement condition table for each of different collision energies.

7. The chromatograph tandem quadrupole mass spectrometer according to claim 1, wherein the measurement condition table creator provides, in the measurement condition table, a field in which the name of the compound included in the compound information table is entered.

8. The chromatograph tandem quadrupole mass spectrometer according to claim 1, wherein the measurement condition table creator, when computing the mass-to-charge ratio range based on the mass-to-charge ratio of the precursor ion, sets a predetermined mass-to-charge ratio as a lower limit of the mass-to-charge ratio range and sets a mass-to-charge ratio obtained by adding another predetermined value to or subtracting another predetermined value from the mass-to-charge ratio of the precursor ion as a upper limit of the mass-to-charge ratio range.

* * * * *